United States Patent [19]

Langer, Jr. et al.

[11] 4,409,409

[45] Oct. 11, 1983

[54] TWO STAGE OLEFIN WAX PROCESS

[75] Inventors: Arthur W. Langer, Jr., Watchung; Gerald Doyle, White House Station; Terry J. Burkhardt, Cranford, all of N.J.; Ralph W. Looney, Baton Rouge, La.

[73] Assignee: Exxon Research and Engineering Co., Florham Park, N.J.

[21] Appl. No.: 386,927

[22] Filed: Jun. 10, 1982

[51] Int. Cl.³ .................................................. C07C 2/74
[52] U.S. Cl. ................................... 585/255; 585/329; 585/524
[58] Field of Search ........................ 585/255, 329, 524

[56] References Cited

U.S. PATENT DOCUMENTS

| | | | |
|---|---|---|---|
| 2,907,805 | 10/1959 | Bestian et al. | 585/524 |
| 2,993,942 | 7/1961 | White et al. | 585/524 |
| 3,441,630 | 4/1969 | Langer et al. | 585/524 |
| 3,629,355 | 12/1971 | Langer et al. | 585/524 |
| 3,647,912 | 3/1972 | Langer et al. | 585/524 |
| 3,655,812 | 4/1972 | Langer | 585/524 |
| 3,662,021 | 5/1972 | Langer | 585/524 |

*Primary Examiner*—Curtis R. Davis
*Attorney, Agent, or Firm*—Richard E. Nanfeldt

[57] ABSTRACT

This invention relates to an improved process for preparing linear olefins and waxes, particularly linear olefin waxes. More particularly, this invention relates to an improved process for polymerizing ethylene to obtain linear olefins and waxes having a number average molecular weight ($\overline{M}_n$) ranging from about 500 to 5000.

The process can be generally described as a two-stage process wherein the first stage is an ethylene oligomerization followed by a second stage metathesis.

Still more particularly, this invention relates to an improved process for polymerizing ethylene to obtain a product comprising at least 70 weight percent linear olefin waxes.

5 Claims, No Drawings

TWO STAGE OLEFIN WAX PROCESS

FIELD OF THE INVENTION

This invention relates to an improved process for preparing linear olefins and waxes, particularly linear olefin waxes. More particularly, this invention relates to an improved process for polymerizing ethylene to obtain linear olefins and waxes having a number average molecular weight ($\overline{M}_n$) ranging from about 500 to 5000.

The process can be generally described as a two-stage process wherein the first stage is an ethylene oligomerization followed by a second stage metathesis.

Still more particularly, this invention relates to an improved process for polymerizing ethylene to obtain a product comprising at least 70 weight percent linear olefin waxes, preferably greater than about 80 weight percent olefin waxes.

PRIOR ART

It has been shown in the prior art (U.S. Pat. Nos. 2,993,942 and 2,907,805) that hydrocarbon lubricating oils having a molecular weight in the range of 80 to 2000 could be prepared by polymerizing ethylene with controlled catalyst compositions, diluents and under controlled temperatures. The catalyst consisted of a transition metal halide and a halogenated aluminum alkyl compound. It has also been found that increased oil yields, catalyst reactivity and improved molecular weight control could be obtained by the addition of a minor amount of a lower alkanol, as a catalyst modifier to the reaction system. Both the modified and unmodified systems described above resulted, under the conditions in the reaction, in the production of major portions of olefins other than linear alpha olefin products, particularly type II (RCH=CHR),

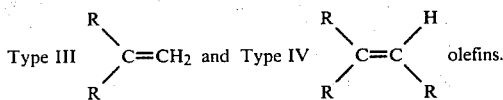

Type III $\begin{array}{c} R \\ \diagdown \\ / \\ R \end{array} C=CH_2$ and Type IV $\begin{array}{c} R \\ \diagdown \\ / \\ R \end{array} C=C \begin{array}{c} H \\ \diagdown \\ \diagdown \\ R \end{array}$ olefins.

Ethylene oligomerization to linear alpha olefins was discovered by one of the inventors of the instant invention, Arthur W. Langer, Jr., who used substantially soluble catalysts comprising tetravalent titanium halides and alkyl aluminum halides under controlled reaction conditions, as described in U.S. Pat. Nos. 3,441,360; 3,647,912; 3,655,812; and 3,662,021. Other Ziegler-type alkyl metal cocatalysts were not useful for oligomerization because they reduced the titanium compound to the heterogeneous Ziegler catalyst which produced high molecular weight polyethylene.

Ethylene oligomerization is a known reaction for making low molecular weight, linear alpha olefins. In a commercial process, Gulf uses AlEt$_3$ at high temperatures and pressures to make predominantly liquid olefins. Langer has developed a catalytic process using an alkyl metal compound and certain Group IVB metal halides which operates at lower temperatures and pressures and produces higher purity olefins at higher rates (U.S. Pat. Nos. 3,647,912; 3,662,021; U.S. Ser. No. 10,527 and others). The Langer process may be controlled to produce higher molecular weight products than the Gulf process such that over 50 percent may be recovered as high quality, high melting, linear alpha olefin wax. Unfortunately, these and other catalytic oligomerization processes produce polymers in which the Flory distribution is $\overline{M}_w/\overline{M}_n=2$. Thus, one can increase the molecular weight of the total product, but one cannot narrow the distribution to further increase selectivity to wax. The same limitation applies to saturated polyethylene waxes in which the chain transfer is done by hydrogen; however, these paraffins are not amenable to further reactions which could increase selectivity.

The oligomerization stage of the instant invention is preferably carried out using Group IVB metal compounds activated by Group II-III metal alkyl or metal hydride compounds as disclosed by one of the present inventors (U.S. Pat. Nos. 3,441,630; 3,629,355; 3,647,912; 3,655,812; 3,662,021; and patent application Ser. Nos. 882,946; 10,527. The titanium catalysts are used below about 80° C., preferably below about 50° C., to minimize the formation of heterogeneous Ziegler catalysts which produce polyethylene rather than oligomers. When making high $\overline{M}_n$ product, the wax fouls the cooling surfaces and makes this system difficult to operate. The most preferred process uses zirconium catalysts such as the halides, alkoxides, dialkylamides, acetylacetonates, carboxylates and mixtures thereof. The halide is preferably chloride or bromide, most preferably chloride. Because of the higher stability of the alkylated tetravalent zirconium compounds with respect to reduction to Ziegler catalysts, these catalysts may be used at temperatures as high as 100° to 200° C. without making excessive amounts of polyethylene by-product. At these temperatures, the wax is soluble and the process is a homogeneous solution process. The zirconium catalysts also are capable of making high molecular weight products (>250 $\overline{M}_n$) at temperatures above 100° C. When used at moderately high ethylene pressure, 500 to 1500 psig, these catalysts make high purity linear alpa olefin products even at the high carbon numbers, in contrast to the AlEt$_3$ process which makes a large amount of branched product in the C$_{20}^+$ fraction.

In the second stage, the metathesis catalyst may be selected from a wide range of systems known in the art since this invention is not restricted to a particular system. Typical catalyst systems have been disclosed in review articles by Robert H. Grubbs, Progress in Inorganic Chemistry, page 1 (1978); R. J. Haines and G. J. Leigh, Chem. Soc. Rev. 4, 155 (1975); J. C. Mol and J. A. Moulijn, Advances in Catalysis 24, 131 (1975); R. L. Banks, Fortschr. Chem. Forsch. 25, 39 (1972); and G. C. Bailey, Cat. Rev. 3, 37 (1969).

SUMMARY OF THE INVENTION

In accordance with this invention, therefore, an improved process for preparing linear olefins, particularly linear alpha olefins and waxes, is provided wherein the improved process comprises a two-stage process for linear, high melting waxes in which the first stage is an oligomerization process in which the total ethylene oligomer product has M$_n$ of 200 to 700. The oligomer has a purity of greater than 90 percent linear alpha olefins in the C$_{12}$–C$_{20}$ fraction, preferably greater than 95 percent and most preferably greater than 98 percent in order to achieve high reactivity and selectivity in the second stage. The second stage is a metathesis process which avoids or minimizes double bond isomerization, thereby producing the highest selectivity to high molecular weight products. By means of this two-stage process, selectivity to C$_{30}^+$ wax reaches 70 to greater than 80 percent compared to a maximum of 40 to 55 percent using the best oligomerization process known at this time. The wax is a linear olefin having the double bond near the center, and the $\overline{M}_n$ of the wax is about 500 to 5000. The double bond may be left in the wax with only small effects on properties or it may be chemically modified to vary wax properties, or alternatively, it may be hydrogenated to further increase melting point and stability.

Any oligomerization process may be used in this invention which is capable of making the molecular weight and linear alpha olefin purity needed in the second stage; that is, a total product $\overline{M}_n$ of about 200 to about 700. Theoretically, the AlEt$_3$ catalyzed oligomerization could be used at lower temperatures which could produce a total product $\overline{M}_n > 200$. However, the oligomerization rate is too low to be economically attractive. The various nickel complex catalysts are suitable when used under conditions which avoid double bond isomerization, but this generally leads to low activity. Furthermore, it has not been possible with nickel catalysts to make high $\overline{M}_n$ total product at high rates.

Ethylene oligomerization is a known reaction for making low molecular weight, linear alpha olefins. In a commercial process, Gulf uses AlEt$_3$ at high temperatures and pressures to make predominantly liquid olefins. Langer has developed a catalytic process using an alkyl metal compound and certain Group IVB metal halides which operates at lower temperatures and pressures and produces higher purity olefins at higher rates (U.S. Pat. Nos. 3,441,630; 3,647,912; 3,662,021; U.S. Ser. No. 10,527 and others). The Langer process may be controlled to produce higher molecular weight products than the Gulf process such that over 50 percent may be recovered as high quality, high melting, linear alpha olefin wax. Unfortunately, these and other catalytic oligomerization processes produce polymers with a Flory distribution which is $\overline{M}_w/\overline{M}_n = 2$. Thus, one can increase the molecular weight of the total product, but one cannot narrow the distribution to further increase selectivity to wax. The same limitation applies to saturated polyethylene waxes in which the chain transfer is done by hydrogen; however, these paraffins are not amenable to further reactions which could increase selectivity.

The oligomerization stage of the instant invention is preferably carried out using Group IVB metal compounds activated by Group II-III metal alkyl or metal hydride compounds as disclosed by one of the present inventors (U.S. Pat. Nos. 3,441,630; 3,629,355; 3,647,912; 3,655,812; 3,662,021; and patent application Ser. Nos. 882,946; 10,527; and patent application Case No. C-659).

The transition metal component used in the oligomerization step may be a halide, an alkoxide or a carboxylate derivative of tetravalent zirconium or hafnium having the general formulas $MX_n(OR')_{4-n}$ and $MX_n(OOCR')_{4-n}$, where $M = Zr$ or $Hf$, $X = Cl$ or $Br$, $n = 0$ to 4 and $R'$ may be an alkyl, aryl, aralkyl or cycloalkyl group. When these components are reacted with the excess aluminum alkyl chlorides, exchange of ligands takes place involving halide, alkyl, alkoxide and carboxylate groups. In addition to exchange of aluminum alkyl groups with transition metal ligands, the aluminum halide groups can also exchange with alkoxy and carboxyl groups on the transition metal compound. These compounds may also be made in situ by reacting the more readily available $MX_4$ with $R'OH$ or $R'COOH$. The alcohols may be unsaturated as in the case where they are the enol forms of carbonyl compounds such as acetylacetone. Typical examples include ZrCl$_4$, ZrBr$_4$, ZrCl$_2$(OEt)$_3$, ZrCl$_2$(OC$_{10}$H$_{21}$)$_2$, ZrBr$_3$OBu, Zr(OPr)$_4$, Zr(OBu)$_4$, ZrCl$_2$(O$\phi$)$_2$, ZrCl$_2$(OOCC$_9$H$_{19}$)$_2$, ZrCl(OOC$\phi$)$_3$, ZrCl$_2$(OE+)$_2$, ZrCl$_3$OOCH$_3$, ZrCl$_2$ glycoxide, Zr acetyl acetonate, ZrCl$_3$-(O-cyclohexyl), HfCl$_4$, HfBr$_4$, Hf(OBu)$_4$, etc.

The metathesis reaction may be run using the neat olefins from the oligomerization stage or solutions in suitable solvents. When run on the total oligomer product, it is necessary to remove some $C_{30}^-$ light ends from the formed wax product but this produces the highest selectivity to wax. Because the light olefin products are of high purity and have large scale uses, it is preferable to separate some of these before carrying out the metathesis. Thus, the feed to metathesis may be any bottoms fraction from topping the oligomer distribution and is preferably $C_8^+$ or higher, and most preferably $C_{14}^+$ or $C_{16}^+$. Typical, but non-limiting examples of metathesis catalysts include CoO.MoO$_3$.Al$_2$O$_3$, Re$_2$O$_7$.Al$_2$O$_3$, WO$_3$.SiO$_2$, Mo(CO)$_6$. Al$_2$O$_3$, WCl$_6$—SnBu$_4$, WCl$_6$—EtAlCl$_2$—EtOH, MoCl$_5$—R$_3$Al—O$_2$ and RAlCl$_2$—R$_4$N$^+$Mo(CO)$_5$Cl$^-$. Metathesis catalysts which minimize double bond isomerization reactions are preferred. Especially preferred metathesis catalyst because of reactivity, selectivity and product purity include Re$_2$O$_7$. Al$_2$O$_3$, CoO.MoO$_3$.Al$_2$O$_3$, WCl$_6$—SnBu$_4$, and RAlCl$_2$—R$_4$N$^+$Mo (CO)$_5$Cl$^-$ as disclosed in U.S. Pat. No. 3,686,136. The C$_{4-14}$ olefins are used as feeds to polymerization, Oxo alcohol synthesis, synthetic lubricants, biodegradable detergents, etc., and the primary product is high quality wax having an M$_n$ of about 500 to about 5000 as is or it can be hydrogenated thereby modifying the properties of the wax. Hydrogenation of the wax can be accomplished by the addition of hydrogen in the presence of a suitable catalyst. Catalysts which minimize cracking and other side reactions are preferred. Massive or supported nickel catalysts such as Harshaw NI-0104 have been found to be particularly suitable.

Ethylene is unique in the instant invention in that other olefins do not respond to give linear alpha olefins. Therefore, it is desirable to use essentially pure ethylene or mixtures of ethylene with inert gases as the feed for the process of this invention. Ethylene feeds containing minor amounts of other olefins may be used provided that the extent of copolymerization does not decrease product linearity below 90 percent.

Polymerization diluent in the oligomerization stage is not a critical feature of this invention. The usable diluents are inert hydrocarbons having about 5 to about 30 carbon atoms and haloaromatic solvents, as well as aliphatics and naphthenics. Less preferred solvents are halogenated aliphatic compounds which, while capable of being employed in the process of preparing linear alpha olefins, require the utilization of higher pressures to achieve average molecular weights of the same order as the preferred solvents. The preferred diluents include hydrocarbon solvents, higher olefin product fractions such as $C_{22}$-$C_{28}$, or $C_{20}^+$ bottoms, aromatics such as benzene, toluene, xylene, tetrahydronaphthalene, etc., aliphatics such as pentane, heptane, isooctane, etc., and naphthenes such as cyclohexane, methylcyclohexane, decahydronaphthalene, etc. The saturated hydrocarbons are most preferred. Recycled product olefins in the range $C_4$-$C_{28}$, preferably $C_{22}$-$C_{28}$, may also be used as diluent with zirconium catalysts which convert more light olefins into linear waxes.

The prior art obtained highly branched olefins (60 percent) when using the soluble titanium catalysts at pressures of 7 to 30 psig., e.g., British Pat. No. 974,577. Ethylene pressures of the instant invention above 3.5 MPa are essential for making linear olefins in high selectivities. Although some variations are permitted, depending upon the catalyst composition, diluent and temperature, the preferred pressures are above about 5.5 to about 10.5 MPa in order to produce commercially attractive yields (at least above 5 weight percent and preferably above 10 weight percent olefins in the reactor effluent) of linear alpha olefins having a purity greater than about 90 mole percent. At very high ethylene pressures, the process may become uneconomical because of the equipment requirements and ethylene recycle. Nevertheless, higher pressures tend to increase the selectivity of the reaction to linear alpha olefins.

The catalyst of this invention enables the process for making linear alpha olefins to be carried out at temperatures of about 50° to about 200° C., preferably between about 100° and about 150° C. The selection of a particular temperature will permit control of the number average molecular weight of the wax product. With zirconium catalysts, temperatures as high as about 200° C. can be used without making excessive amounts of polyethylene. However, the high temperatures cause product isomerization and require higher ethylene pressures to prevent copolymerization, which makes them less attractive. The preferred temperatures to obtain high purity linear alpha olefins with zirconium catalysts are between about 50° to about 200° C. and more preferably between about 75° to about 150° C. to obtain total product $\overline{M}_n$ greater than 250.

Reaction times of the oligomerization stage are not particularly critical when operating under the preferred conditions and they will normally be in the range of 0.1 to 5 hours to obtain product concentrations greater than 5 percent by weight in the diluent. The process may be carried out in batch or continuous operation. However, high product purity and high concentration are achieved most easily in batch reactions or in continuous systems operating under essentially plug flow conditions. A reactor may consist of a long pipe through which the diluent and catalyst flow with ethylene being introduced at many points along the pipe to maintain the desired ethylene concentration. In such a system, monomer concentration need not be constant but may be controlled differently in different sections of the reactor to achieve the best balance of activity, molecular weight and product purity. Stirred tank reactors may be operated in series to approach plug flow.

The metathesis stage of the process is preferably carried out by collecting $C_{16}^+$ bottom fractions from the first stage oligomerization process and dissolving this $C_{16}^+$ bottoms fraction in a suitable solvent such as chlorobenzene solvent. Suitable metathesis catalyst such as $RAlCl_2$—$R_4N^+Mo(CO)_5Cl^-$ or $WCl_6$—$SnBu^4$ in hexane is charged into the solution of the $C_{16}^+$ bottoms fraction and solvent and the metathesis reaction is carried out at about 50° to about 100° C., preferably about 75° C., for a sufficient period of time (e.g., two hours) so as to increase the wax selectivity to over 70 percent. The product from the metathesis stage is quenched with methanol, then filtered and washed to remove catalyst and subsequently dried. The melted wax is then filtered to remove insoluble catalyst residues.

The following examples are submitted in order to more particularly point out applicant's invention, but are not to be construed as limitations on the scope of the instant invention as described in the appended claims.

EXAMPLE 1

Oligomerization of ethylene was done in a 1-liter autoclave with magnetic stirring using 0.2 mmole $EtAlCl_2$ (EADC), 0.05 mmole $Et_2AlCl$ (DEAC) and 0.05 mmole $Zr(OPr)_4$ in 350 ml. n-heptane at 110° C., 1000 psig ethylene pressure for 30 minutes. A sample taken for G.C. analysis showed a yield of 135 g. (based on an internal standard), $\overline{M}_n=242$, and the purity measured on the $C_{12-20}$ fraction was 98.6 percent linear alpha olefin.

The oligomerization reaction product was cooled to 90° C. and ethylene was vented. A portion of metathesis catalyst was charged (3 mmoles $(C_8H_{17})_3NMe^+Mo(CO)_5Cl^-$ and 24 mmoles $EtAlCl_2$) and stirred 2.5 hours at 60° to 80° C. with little signs of reaction. Addition of 4 mmoles $Bu_4N^+Mo(CO)_5Cl^-$ gave a rapid evolution of ethylene. After another hour, a G.C. sample showed the same molecular weight distribution (based on $C_{10-30}$) as in the oligomerization ($\overline{M}_w/\overline{M}_n=2$), but $\overline{M}_n=344$. Thus, the selectivity to $C_{30}^+$ wax was increased from 41 weight percent at $\overline{M}_n=242$ to 61 weight percent at $\overline{M}_n=344$.

EXAMPLE 2

The oligomerization procedure of Example 1 was followed except that the millimolar catalyst amounts were 0.24 EADC/0.06 DEAC/0.06 $Zr(OPr)_4$ and the run temperature was 100° C. After 30 minutes, 0.2 mmole methoxyethanol in 20 ml. chlorobenzene was added to quench the oligomerization catalyst and a G.C. sample was taken which analyzed for 211 g. product, 254 $\overline{M}_n$ and 99.1 percent purity.

Ethylene and light ends were flashed at 100° C. and analysis of the trapped light ends showed that $C_{4-8}$ olefins were present.

A metathesis catalyst was charged (2 mmoles $Bu_4N^+Mo(CO)_5Cl^-$ plus 16 mmoles $MeAlCl_2$ in 80 ml. chlorobenzene) at 60° C. and the mixture allowed to react 27 minutes. A G.C. sample showed that $\overline{M}_n$ had increased to 413 and purity was 98.4 percent linear olefins.

The reactor product was crystallized twice from methanol and vacuum dried, yielding 142 g. wax having 710 $\overline{M}_n$ (by vapor phase osmometry). G.C. analysis showed small amounts of light ends between $C_{12}$ and $C_{28}$ were still present in the product. Only trace amounts of odd-numbered olefins were present, showing that very little isomerization occurred during metathesis.

EXAMPLE 3

The oligomerization procedure of Example 2 was followed except that the millimolar quantities of catalyst were 0.06 EADC/0.06 DEAC/0.06 $ZrCl_2(OPr)_2$ in one run and 0.04/0.04/0.04 in a second run. The products were combined, water washed twice at 80° to 90° C. to remove catalyst, insoluble polyethylene (3.73 g.) was removed at 100° C., and water plus light ends were stripped out by nitrogen sweeping at 100° to 125° C. The $C_4$ and $C_6$ olefins were largely removed together with some of the $C_8$, $C_{10}$ and $C_{12}$. The total product $M_n$ was 259 before removal of light ends and an estimated 330 $M_n$ after stripping.

A sample of the above product (113 g.) was purged with nitrogen while heating to about 115° C. at which temperature the wax had melted to a clear liquid. At 125° C., 5 g. Re$_2$O$_7$.Al$_2$O$_3$ catalyst (activated at 550° C., 1 hr, air, 1 hr, N$_2$) (9.2 percent Re) was added. There was an immediate gas evolution which continued for five hours. The recovered product (88.5 g.) was a hard wax having $\overline{M}_n = 778$ (by VPO).

EXAMPLE 4

Ethylene oligomerization was carried out in a 1-gallon continuous pilot plant at 120° C. and 1400 psig. The molar ratio of catalyst components was 4 EADC/1 DEAC/1 Zr(OPr)$_4$ and the Zr(OPr)$_4$ feed rate was 0.245 g/hr. Under lined out conditions, the product concentration was 25.2 weight percent in the heptane solvent, the ethylene conversion was 45.2 percent, the oligomerization rate was 30,200 g. oligomer/g. Zr(OPr)$_4$/hr, the product $\overline{M}_n = 232$, and the purity was 99.0 percent.

Metathesis was carried out using 75 g. of C$_{16}$+ bottoms fraction from the above oligomerization. The wax was dissolved in 30 ml. of chlorobenzene at 75° C., then 1.54 g. Bu$_4$N+Mo(CO)$_5$Cl− and 2.71 g. MeAlCl$_2$ were added. After two hours at 75° C., the product was quenched with methanol, filtered and washed to remove catalyst, dried and the melted wax was filtered to remove insoluble catalyst residues.

A sample of the metathesized wax was dissolved in heptane and hydrogenated six hours at 200° C. and 1500 psig hydrogen using Harshaw 0104 nickel catalyst. The solution containing the hydrogenated wax was decanted from the solid catalyst particles then the solvent was removed by heating to about 100° C.

Without further purification or fractionation, the total hydrogenated wax sample had the following properties. Congealing Point 220+° F., Melt Dropping Point 235° F., Penetration at 77° F.=1, at 100° F.=4, and Viscosity at 300° F.=9.4 cp. These properties are equivalent to, or superior to the competitive commercial waxes.

EXAMPLE 5

Added to 100 ml. heptane were 74.4 g. of C$_{16}$+ alpha olefins from the oligomerization process, then the heptane was distilled off to a 114° C. overhead temperature to dry the alpha olefins. The temperature was adjusted to 110° C. and 0.104 g. of WCl$_6$ was added to the reactor followed by 0.077 mmoles of AlEt$_2$Cl and 0.26 mmoles of SnBu$_4$. After stirring for two hours, at 115° C., a GC sample showed that 84 weight percent of the initial charge of the C$_{20}$ alpha olefin had been metathesized indicating a total conversion of lower molecular olefins to a higher molecular weight product of 84 weight percent.

What is claimed is:
1. A process for preparing linear waxes having an $\overline{M}_n$ of about 500 to about 5000 which comprises the steps of:
   (a) oligomerizing ethylene to an ologomerization product having an $\overline{M}_n$ of about 200 to 700;
   (b) metathesizing said oligomerization product to form a linear olefin wax; and
   (c) removing from said linear olefin wax essentially all products having a carbon number of less than about C$_{30}$.
2. A process according to claim 1 further including hydrogenating said linear olefin wax.
3. A process according to claim 1 wherein a catalyst system for said oligomerization is a Group IVB metal compound activated by a Group II-III metal alkyl or metal hydride compound.
4. A process according to claim 3 wherein said Group IVB metal compound has the formula:

$$MX_n(OR')_{4-n}$$

wherein M is Zr or Hf, X is Cl or Br, n is 0 to 4 and R' is selected from the groups consisting of alkyl, aryl, aralkyl and cycloalkyl.

5. A process according to claim 1 wherein a catalyst for said metathesis process is selected from the group consisting of CoO.MoO$_3$.Al$_2$O$_3$, Re$_2$O$_7$.Al$_2$O$_3$, WO$_3$.-SiO$_2$, Mo(CO)$_6$.Al$_2$O$_3$, WCl$_6$.SnBu$_4$, WCl$_6$—EtAlCl$_2$—EtOH, MoCl$_5$—R$_3$Al—O$_2$ and RAlCl$_2$—R$_4$N+Mo(CO)$_5$Cl−.

* * * * *